United States Patent [19]

Glover et al.

[11] Patent Number: 4,829,052

[45] Date of Patent: May 9, 1989

[54] SERINE PROTEASE INHIBITORS

[75] Inventors: George I. Glover, Creve Coeur; Charles A. McWherter, Ballwin; Charles S. Schasteen, University City, all of Mo.

[73] Assignee: Monsanto Company, St. Louis, Mo.

[21] Appl. No.: 45,833

[22] Filed: May 8, 1987

Related U.S. Application Data

[63] Continuation-in-part of Ser. No. 873,014, Jun. 11, 1986, abandoned.

[51] Int. Cl.$^4$ .................. A61K 37/02; C07K 7/10
[52] U.S. Cl. ............................... 514/12; 530/324
[58] Field of Search ...................... 530/324; 514/12

[56] References Cited

PUBLICATIONS

Wieczorek et al., Biochemical and Biophysical Research Communications, vol. 126, No. 2, pp. 646–652 (1985).

Kupryszewski et al., Experientia, vol. 41, pp. 1422–1423 (1985).

Rudinger, Peptide Hormones, Parsons (Ed.), U Park Press, Baltimore, pp. 1–7 (1976).

Joubert, F. J., "Trypsin Isoinhibitors from Momordica Repens Seed" 1984 *Phytochemistry*, vol. 23, No. 7, pp. 1401–1405.

*Primary Examiner*—Delbert R. Phillips
*Assistant Examiner*—Christina Chan
*Attorney, Agent, or Firm*—Dennis R. Hoerner, Jr.; Larry R. Swaney; J.W. Williams, Jr.

[57] ABSTRACT

Synthetic polypeptides are disclosed which exhibit potent serine protease inhibition. Methods and compositions useful for treating conditions caused by unwanted serine protease activity are also disclosed.

18 Claims, 4 Drawing Sheets

SERINE PROTEASE INHIBITORS

This is a continuation-in-part application of co-pending application Ser. No. 873,014 filed June 11, 1986, now abandoned.

In its broadest aspect, the present invention relates to enzyme inhibitors. More particularly, it relates to novel polypeptid-es which exhibit inhibitory activity toward serine proteases.

The mechanistic class of proteolytic enzymes known as serine proteases is widely distributed in nature having been identified in animals, microbes and insects. The assignment of members to this class was originally made on the basis of their enzymatic mechanisms. Subsequently, members of this class have demonstrated a great deal of sequence and structural homology. Serine proteases are typified by a catalytic triad consisting of aspartic acid, histidine and serine at the active site. Serine proteases can be easily identified since the active site serine can be irreversibly and covalently modified by diisopropylfluorophosphate.

Serine protease inhibitors have been found in microbes and in the tissues and fluids of plants, animals, insects and other organisms. The naturally occurring serine protease inhibitors are usually, but not always, polypeptides and proteins which have been classified into families primarily on the basis of the disulfide bonding pattern and the sequence homology of the reactive site. The reactive site is defined as the portion of the primary sequence that directly interacts with the protease. Studies have indicated that most inhibitors inhibit by a common mechanism in which the inhibitor is actually a poor substrate which is tightly bound and only very rarely experiences the catalytic hydrolysis of a particular bond within the reactive site. However, if the pH is drastically changed from neutrality hydrolysis of the reactive site peptide bond occurs.

In addition to their normal physiological function, serine proteases have been implicated in a number of pathological conditions in humans including pulmonary emphysema, various clotting disorders and inflammatory processes. One illustration of the importance of the catalytic activity of serine proteases is provided by the role of human neutrophil elastase and one of its natural inhibitors, $\alpha$-1-proteinase inhibitor ($\alpha$-P1), in the pathogenesis of emphysema. In the lungs of healthy individuals there is a balance between the levels of elastase and its inhibitors. The elastase serves in the repair and turnover of connective tissues (elastin) and the $\alpha$-1-proteinase inhibitor is involved in the regulation and clearance of elastase. The term elastin refers to a heterogeneous, highly cross-linked and highly insoluble polypeptide, that is the main component of elastic connective tissue in the body. Disruption of the elastase/$\alpha$-1-proteinase inhibitor balance leads to increased elastin degradation and, hence, to elastic tissue destruction. New elastin can be synthesized but the proper network of elastic fibers which is laid down during lung development is not achieved. A prolonged imbalance leads to an irreversible dilation of pulmonary airways and damage to the respiratory tissues of the lung, a condition known as pulmonary emphysema.

This imbalance may occur in a number of ways. An example is the case of familial emphysema first identified in Scandinavia. Individuals found to have a homozygous genetic deficiency for active forms of serum $\alpha$-1-proteinase inhibitor have been shown to be more likely to develop emphysematous symptoms, especially when exposed to other risk factors such as cigarette smoking. As another example, oxidants from the condensate of cigarette smoke have been shown to drastically reduce the elastase binding affinity of $\alpha$-1-proteinase inhibitor by oxidizing a methionine residue within the reactive site. Furthermore, the serum of smokers has been shown to have dramatically higher levels of oxidized $\alpha$-1-proteinase inhibitor when compared to non-smokers. It has been concluded that the balance has been disrupted by the inactivation of the inhibitor. A final example involves both elevated levels of elastase and simultaneously lower levels of functional $\alpha$-1-proteinase inhibitor. The inflammatory response to foreign particulate matter from air pollution or cigarette smoke leads to elevated levels of polymorphonuclear leukocytes in the lungs. These cells disrupt the protease/protease inhibitor balance by secretion of proteolytic enzymes, e.g., elastase. They also secrete oxidants including myeloperoxidase which appear to oxidatively inactive $\alpha$-1-proteinase inhibitor. Thus, imbalances created through the removal of a control mechanism or through the prolonged induction of elevated levels of elastase eventually leads to an undesirable pathological situation, damage to connective tissue and diminished pulmonary function.

$\alpha$-1-Proteinase inhibitor (antitrypsin, AT) is a single-chain glycoprotein of MW 51,000 with 394 amino acids with no disulfide bridges and 3 oligosaccharide side chains that is present in human serum at 130 mg/100 ml or 23.6 [2 M. It easily diffuses into tissue spaces and forms a 1:1 complex with a target protease, principally neutrophil elastase. The enzyme/inhibitor complex is then rapidly removed from circulation and catabolized by the liver and spleen. Human AT was originally named antitrypsin because of its ability to inactivate pancreatic trypsin.

There are many practical problems in the use of naturally-occuring mammalian serine protease inhibitors, or related materials, as therapeutic agents. The relatively large naturally occuring mammalian serine protease inhibitors pose a problem since large polypeptides can be more difficult to produce and administer to the patient than smaller polypeptides. These naturally occurring inhibitors lack stabilizing disulfide bridges and are heat labile. Also, the oligosaccharide side chains have been shown to have an effect on the life-lime of the inhibitors in vivo. Thus, the production of these inhibitors with the proper oligosaccharide component is another serious difficulty in their use as therapeutic agents.

The description involving elastase given above furnishes but one example of a situation where the control of serine protease activity is useful and desirable. The scope of this invention includes, but is by no means limited to, inhibition of human elastase.

It is therefore the goal of the present invention, in its broadest aspect, to provide novel serine protease inhibitors.

Accordingly, it should be recognized that this invention is applicable to the control of catalytic activity of serine proteases in any appropriate situation including, but not necessarily limited to, medicine, biology, agriculture, and microbial fermentation.

These and other objects and advantages of the present invention will be recognized by those skilled in the art from the following description and representative examples.

DESCRIPTION OF THE INVENTION

The present invention provides synthetic polypeptides which exhibit inhibitory activity toward target serine proteases and a process for preparing same. Target serine proteases are those which exhibit a strong preference for amino acid residues adjacent to the site of cleavage in the amino-terminal direction of peptide substrates. Exemplary of such serine proteases are elastase and cathepsin G. More particularly, the present invention provides synthetic serine protease inhibitors having the following amino acid sequence:

Arg—Val—Cys—Pro—X—Ile—Leu—Met—Lys—Cys—Lys—

Lys—Asp—Ser—Asp—Cys—Leu—Ala—Glu—Cys—Val—

Cys—Leu—Glu—His—Gly—Tyr—Cys—Gly and homologous variations thereof in which X represents an amino acid other than arginine or lysine which is adapted to impart inhibitory activity towards a target serine protease. By "synthetic" is meant that the polypeptides are not naturally-occuring compounds.

The inhibitors of the present invention possess certain qualities which make them quite practical. The short sequence of these polypeptides (29 to 32 amino acid residues) facilitates their production, especially by the methods of chemical synthesis. The large number of half-cystine residues relative to the total number of residues indicates a high degree of cross-linking through disulfide bond formation. While the particular pairing of half-cystine residues is not known at this time, the polypeptide inhibitors of the present invention can be easily folded to their bio- logically-active form as described hereinafter. It is likely that these polypeptides are rigid and compactly folded, a feature that generally confers stability on polypeptides and proteins.

All polypeptide structures represented in the following description and claims are shown in conventional format wherein the amino group at the N-terminus appears to the left and the carboxyl group at the C-terminus at the right. Unless noted otherwise all amino acids are L-amino acids. The nomenclaure for the naturally occurring amino acids found in proteins and comprising the polypeptide inhibitors of the present invention is as follows: alanine (Ala;A), aspargine (Asn;N), aspartic acid (Asp;D), arginine (Arg;R), cysteine or half-cystine (Cys;C), glutamic acid (glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W) tyrosine (Tyr;Y), and valine (Val;V).

All of the chemical, biological, medical and technical words, phrases, symbols and nomenclature are common to those experienced in the life sciences and these words, phrases, symbols and nomenclature have experienced common usage in both textbooks and the original scientific literature. Definitions can be found by reference to textbooks on the appropriate subject or in the recommendations of the IUPAC-IUB commission on biochemical nomenclature, "Biochemical Nomenclature and Related Documents", Biochemical Society, P.O. Box 32, Commerce Way, Colchester, Essex CO2 8HP England.

Exemplary polypeptide inhibitors of the of Schecter and Berger (Biochem. Biophys. Res. Commun. 27, 157 [1967]) is used in Table I to denote the relative positions of the residues with respect to the reactive site peptide bond. In this notation P1, P2, P3, etc., refers to the series of residues proceeding away from the reactive site bond in the direction of the amino terminus one residue at a time. A similar definition for P1', P2', P3', etc., obtains, except that the direction is toward the carboxyl terminus.

The inhibitors of the present invention are related to the family of trypsin inhibitors from squash plants shown in Table II. The squash family of trypsin inhibitors is a recently discovered group of inhibitors found in the seeds of *Cucurbitacea* plants (Wieczorek et al., *Biochem. Biophys. Res. Comm.*, 126, 646–652, 1985). Thus far, seven unique members have been characterized by amino acid sequencing and equilibrium association constants with bovine trypsin have been determined for six of these members, see Table II.

The amino and carboxy terminal extensions give an indication that the naturally-occurring trypsin inhibitors from squash are produced by proteolytic processing of larger molecular weight precursors. This phenomenon has been observed with respect to other serine protease inhibitors from plant sources. This is of importance because many proteins and polypeptides, more readily fold to their biologically-active forms in their precursor forms and are subsequently processed to yield the smaller peptide or protein. (Steiner et al., *Proc.Natl. Acad. Sci., USA*, 60, 622–629, 1968). Thus, prior to the present discovery it was unknown whether the protease inhibitors of the present invention could be synthesized in their mature form and thereafter assume their biologically-active conformation.

By analogy with the squash famiy of trypsin inhibitors, the reactive site can be identified as comprising residues P5 through P5' inclusive. It should be recognized that this assignment is not precise, but its precise delineation is not important for the purpose of the present invention. Rather, it is required that some of the residues within the designated reactive site play a role in determining the affinity and selectivity of the inhibitory activity of these polypeptides. Presumably, this would occur through the detailed molecular interactions between the reactive site residues of the inhibitor and the active site residues of the target serine protease.

TABLE I

| Inhibitor Peptide | P8 | P7 | P6 | P5 | P4 | P3 | P2 | P1 | P1' | P2' | P3' | P4' | P5' | | | | | | | Framework | | | | | | | | | | |
|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | |
| 1 | H | E | | R | V | C | P | I | I | L | M | K | C | K | K | D | S | D | C | L | A | E | C | V | C | L | E | H | I | — | G | Y | C | G |
| 2 | | | | R | V | C | P | I | I | L | M | K | C | K | K | D | S | D | C | L | A | E | C | V | C | L | E | H | I | — | G | Y | C | G |
| 3 | | | E | R | V | C | P | I | I | L | M | K | C | K | K | D | S | D | C | L | A | E | C | L | C | L | E | H | I | — | G | Y | C | G |
| 4 | H | E | | R | V | C | P | I | I | L | M | K | C | K | K | D | S | D | C | L | A | E | C | V | C | L | E | D | I | — | G | Y | C | G |
| 5 | | | | M | M | C | P | I | I | L | M | E | C | K | H | D | S | D | C | L | A | D | G | V | C | L | E | H | I | — | G | E | C | G |
| 6 | | | E | M | M | C | P | I | I | L | M | E | C | K | K | D | S | D | C | L | P | E | E | L | C | L | E | H | I | — | G | G | C | G |
| 7 | H | E | | R | V | C | P | I | V | L | M | K | C | K | K | D | S | D | C | L | A | E | C | V | C | L | E | H | I | — | G | Y | C | G |
| 8 | | | | R | V | C | P | I | V | L | M | K | C | K | K | D | S | D | C | L | A | E | C | V | C | L | E | H | I | — | G | Y | C | G |
| 9 | | | E | R | V | C | P | I | V | L | M | K | C | K | K | D | S | D | C | L | A | E | C | L | C | L | E | H | I | — | G | Y | C | G |
| 10 | H | E | | R | V | C | P | I | V | L | M | K | C | K | K | D | S | D | C | L | A | E | C | V | C | L | E | D | I | — | G | Y | C | G |
| 11 | | | | M | M | C | P | I | V | L | M | E | C | K | H | D | S | D | C | L | A | D | G | V | C | L | E | H | I | — | G | E | C | G |
| 12 | | | E | M | M | C | P | I | V | L | M | E | C | K | K | D | S | D | C | L | P | E | E | L | C | L | E | H | I | — | G | G | C | G |
| 13 | H | E | | R | V | C | P | V | V | L | M | K | C | K | K | D | S | D | C | L | A | E | C | V | C | L | E | H | I | — | G | Y | C | G |
| 14 | | | | R | V | C | P | V | V | L | M | K | C | K | K | D | S | D | C | L | A | E | C | V | C | L | E | H | I | — | G | Y | C | G |
| 15 | | | E | R | V | C | P | V | V | L | M | K | C | K | K | D | S | D | C | L | A | E | C | L | C | L | E | H | I | — | G | Y | C | G |
| 16 | H | E | | R | V | C | P | V | V | L | M | K | C | K | K | D | S | D | C | L | A | E | C | V | C | L | E | D | I | — | G | Y | C | G |
| 17 | | | | M | M | C | P | V | V | L | M | E | C | K | H | D | S | D | C | L | A | D | G | V | C | L | E | H | I | — | G | E | C | G |
| 18 | | | E | M | M | C | P | V | V | L | M | E | C | K | K | D | S | D | C | L | P | E | E | L | C | L | E | H | I | — | G | G | C | G |
| 19 | H | E | | R | V | C | P | F | I | L | M | K | C | K | K | D | S | D | C | L | A | E | C | V | C | L | E | H | I | — | G | Y | C | G |
| 20 | | | | R | V | C | P | F | I | L | M | K | C | K | K | D | S | D | C | L | A | E | C | V | C | L | E | H | I | — | G | Y | C | G |
| 21 | | | E | R | V | C | P | F | I | L | M | K | C | K | K | D | S | D | C | L | A | E | C | L | C | L | E | H | I | — | G | Y | C | G |
| 22 | H | E | | R | V | C | P | F | I | L | M | K | C | K | K | D | S | D | C | L | A | E | C | V | C | L | E | D | I | — | G | Y | C | G |
| 23 | | | | M | M | C | P | M | I | L | M | E | C | K | H | D | S | D | C | L | A | D | G | V | C | L | E | H | I | — | G | E | C | G |
| 24 | | | E | M | M | C | P | M | I | L | M | E | C | K | K | D | S | D | C | L | P | E | E | L | C | L | E | H | I | — | G | G | C | G |
| 25 | H | E | | R | V | C | P | M | I | L | M | K | C | K | K | D | S | D | C | L | A | E | C | V | C | L | E | H | I | — | G | Y | C | G |
| 26 | | | | R | V | C | P | M | I | L | M | K | C | K | K | D | S | D | C | L | A | E | C | V | C | L | E | H | I | — | G | Y | C | G |
| 27 | | | E | R | V | C | P | M | I | L | M | K | C | K | K | D | S | D | C | L | A | E | C | L | C | L | E | H | I | — | G | Y | C | G |
| 28 | H | E | | R | V | C | P | L | I | L | M | K | C | K | K | D | S | D | C | L | A | E | C | V | C | L | E | D | I | — | G | Y | C | G |
| 29 | | | | M | M | C | P | L | I | L | M | E | C | K | H | D | S | D | C | L | A | D | G | V | C | L | E | H | I | — | G | E | C | G |
| 30 | | | E | M | M | C | P | L | I | L | M | E | C | K | K | D | S | D | C | L | P | E | E | L | C | L | E | H | I | — | G | G | C | G |
| 31 | H | E | | R | V | C | P | L | I | L | M | K | C | K | K | D | S | D | C | L | A | E | C | V | C | L | E | H | I | — | G | Y | C | G |
| 32 | | | | R | V | C | P | A | I | L | M | K | C | K | K | D | S | D | C | L | A | E | C | V | C | L | E | H | I | — | G | Y | C | G |
| 33 | | | E | R | V | C | P | A | I | L | M | K | C | K | K | D | S | D | C | L | A | E | C | L | C | L | E | H | I | — | G | Y | C | G |
| 34 | H | E | | R | V | C | P | A | I | L | M | K | C | K | K | D | S | D | C | L | A | E | C | V | C | L | E | D | I | — | G | Y | C | G |
| 35 | | | | M | M | C | P | A | I | L | M | E | C | K | H | D | S | D | C | L | A | D | G | V | C | L | E | H | I | — | G | E | C | G |
| 36 | | | E | M | M | C | P | A | I | L | M | E | C | K | K | D | S | D | C | L | P | E | E | L | C | L | E | H | I | — | G | G | C | G |
| 37 | H | E | | R | V | C | P | V | I | L | M | K | C | K | K | D | S | D | C | L | A | E | C | V | C | L | E | H | I | — | G | Y | C | G |
| 38 | | | | R | V | C | P | V | I | L | M | K | C | K | K | D | S | D | C | L | A | E | C | V | C | L | E | H | I | — | G | Y | C | G |
| 39 | | | E | R | V | C | P | V | I | L | M | K | C | K | K | D | S | D | C | L | A | E | C | L | C | L | E | H | I | — | G | Y | C | G |
| 40 | H | E | | R | V | C | P | V | I | L | M | K | C | K | K | D | S | D | C | L | A | E | C | V | C | L | E | D | I | — | G | Y | C | G |
| 41 | | | | | R | C | P | V | I | L | M | K | C | K | K | D | S | D | C | L | A | E | C | V | C | L | E | H | I | — | G | Y | C | G |
| 42 | | | | | R | C | P | V | I | L | Nle² | K | C | K | K | D | S | D | C | L | A | E | C | V | C | L | E | H | I | — | G | Y | C | G |
| 43 | | | | | R | C | Hyp³ | V | S | L | M | K | C | K | K | D | S | D | C | L | A | E | C | V | C | L | E | H | I | — | G | Y | C | G |
| 44 | | | | | R | C | G | V | I | L | L | K | C | K | K | D | S | D | C | L | A | E | C | V | C | L | E | H | I | — | G | Y | C | G |
| 45 | | | | | R | C | P | V | I | L | M | K | C | K | K | D | S | D | C | L | A | E | C | V | C | L | E | H | I | — | G | Y | C | G |
| 46 | | | | | R | C | P | A | A | L | M | K | C | K | K | D | S | D | C | L | A | E | C | V | C | L | E | H | I | — | G | Y | C | G |
| 47 | | | | | R | P | P | V | V | L | M | K | C | K | K | D | S | D | C | L | A | E | C | V | C | L | E | H | I | — | G | Y | C | G |
| 48 | | | | | R | P | C | V | V | L | M | K | C | K | K | D | S | D | C | L | A | E | C | V | C | L | E | H | I | — | G | Y | C | G |
| 49 | | | | | R | C | C | V | I | L | M | K | C | K | K | D | S | D | C | L | A | E | C | V | C | L | E | H | I | — | G | Y | C | G |
| 50 | | | | | R | V | P | C | A | L | M | K | L | K | K | D | S | D | C | L | A | E | C | V | C | L | E | H | I | — | G | Y | C | G |
| 51 | | | | | R | V | C | G | I | L | M | K | C | K | K | D | S | D | C | L | A | E | C | V | C | L | E | H | I | — | G | Y | C | G |

TABLE I-continued

| Inhibitor Peptide | P8 | P7 | P6 | P5 | P4 | P3 | P2 | Reactive Site P1 | P1' | P2' | P3' | P4' | P5' | | | | | | Framework | | | | | | |
|---|---|---|---|---|---|---|---|---|---|---|---|---|---|---|---|---|---|---|---|---|---|---|---|---|---|
| 52 | H | E | E | R | V | C | P | G | I | L | M | K | C | K | D | S | D | C | L | L | A | E | C | V | C | L | E | H | — | G | Y | C | G |
| 53 | | | | R | V | C | P | G | I | L | M | E | C | K | K | D | S | D | C | L | L | A | E | C | V | C | L | E | H | — | G | Y | C | G |
| 54 | | | | R | V | C | P | G | I | L | M | E | C | K | K | D | S | D | C | L | L | A | E | C | I | C | L | E | H | — | G | Y | C | G |
| 55 | H | E | E | R | V | C | P | G | I | L | M | K | C | K | H | D | S | D | C | L | L | A | D | C | V | C | L | E | D | — | G | Y | C | G |
| 56 | | | | M | M | C | P | G | I | L | M | K | C | K | H | D | S | D | C | L | P | G | C | V | C | L | E | H | I | E | Y | C | G |
| 57 | | | | M | | | | | | | | | | | | | | | | | | | | | | | | | | | | | | |

¹gap inserted for homology comparison
²Nle represents norleucine
³Hyp represents hydroxyproline

TABLE II
TRYPSIN INHIBITORS FROM SQUASH SEED

| | | Reactive Site | | | | | | | | | | | | | Framework | | | | | | | | | | | | | $K_a, M^{-1}$ |
|---|---|---|---|---|---|---|---|---|---|---|---|---|---|---|---|---|---|---|---|---|---|---|---|---|---|---|---|---|
| | | R | V | C | P | R | I | L | M | K | C | K | K | D | S | D | C | L | A | E | C | V | C | L | E | H | —[1] G Y C G | $6.8 \times 10^{11}$ |
| H E E | | R | V | C | P | R | I | L | M | K | C | K | K | D | S | D | C | L | A | E | C | V | C | L | E | H | — G Y C G | $5.9 \times 10^{10}$ |
| | | R | V | C | P | R | I | L | M | E | C | K | K | D | S | D | C | L | A | E | C | V | C | L | E | H | — G Y C G | $3.2 \times 10^{11}$ |
| | | R | V | C | P | K | I | L | M | E | C | K | K | D | S | D | C | L | A | E | C | I | C | L | E | H | — G Y C G | $8.5 \times 10^{11}$ |
| H E E | | R | V | C | P | K | I | L | M | E | C | K | K | D | S | D | C | L | A | E | C | I | C | L | E | H | — G Y C G | $1.3 \times 10^{11}$ |
| | | M | V | C | P | K | I | L | M | K | C | K | H | D | S | D | C | L | L | D | C | V | C | L | E | D | I G Y C G | $9.5 \times 10^{11}$ |
| | | M | M | C | P | R | I | L | M | K | C | K | H | D | S | D | C | L | P | G | C | V | C | L | E | H | I E Y C G | NR |

Amino acid sequence of the squash family of inhibitors. Ka is the association equilibrium constant with trypsin (Wieczorek et al, Biochem. Biophys. Res. Comm. 126, 646-652 (1985)).
NR = Not Reported
[1] represents gap inserted for homology comparison.

The polypeptide inhibitors can be made to exhibit inhibitory activity toward a target serine protease by insertion of a suitable amino acid residue in the P1 position. For example, suitable P1 amino acids for preparing an elastase inhibitor include, but are not necessarily limited to, isoleucine, leucine, norleucine (Nle), valine, norvaline (Nva), methionine, phenylalanine and alanine.

Analysis of the published or experimentally determined preferences of the target serine protease for amino acid type at the P1 position of substrates and inhibitors will direct the selection of a P1 substitution to prepare an inhibitor of that target protease. The relative preferences of the target serine protease for various amino acids at the P1 position can be easily determined using the following method.

Figure 1:
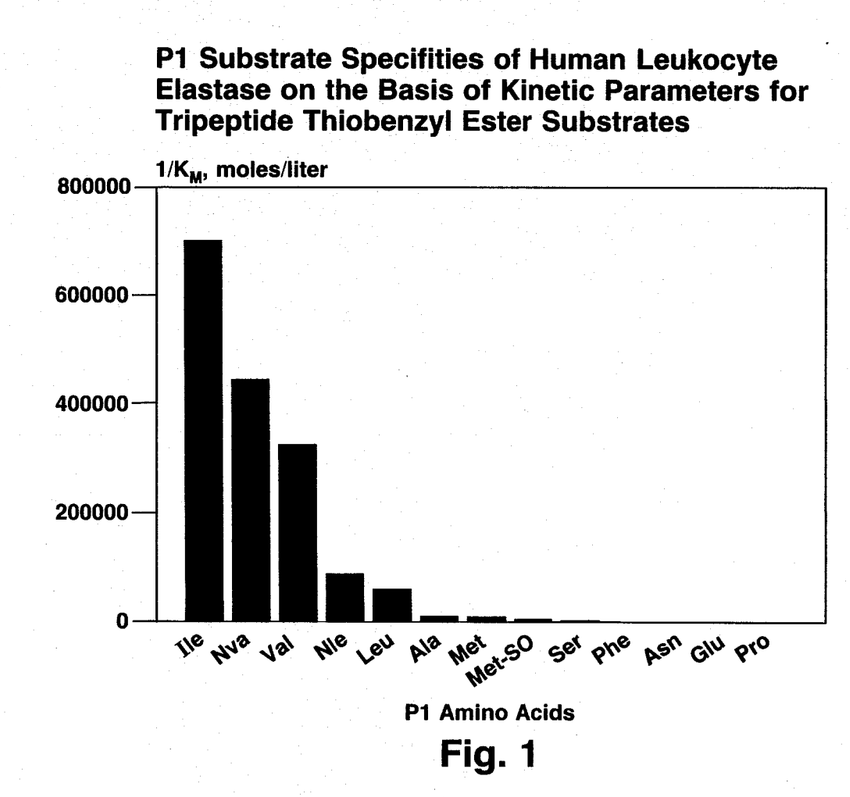
FIG. 1 is a graphical representation of the preferences of human leukocyte elastase for amino acids at the position just amino terminal to the site of cleavage. This position is called the P1 position and is discussed in more detail in the specification.

A number of small peptide derivatives of the form X-Y-aa-Z are prepared where X and Y are amino acids that are the same in each of the derivatives and aa is the P1 amino acid that is varied. The Z group represents a chromogenic leaving group that is split off by the enzyme. Usually, the amino terminus of the polypeptides will be blocked to prevent end-effects. The Michaelis-Menten kinetic parameters are then determined for each member of the series using standard techniques. The binding preference of the enzyme for the P1 substrate is of most interest. Under conditions in which the equilibrium of substrate binding to the enzyme is rapid with respect to dissociation of product (turnover) the inverse of $K_m$, the well known Michaelis constant, is indicative of the substrate-enzyme association constant. Thus by examining $1K/_m$ for a series of peptide derivatives differing only in the P1 amino acid on can readily determine the P1 amino acid substrate binding preferences of a particular enzyme. As an example, FIG. 1 illustrates the published data with respect to P1 substrate preferences for human leukocyte elastase (Harper et al., *Biochemistry*, 23, 2995-3002, 1984). A series of tripeptide thiobenzyl ester substrates of the form Boc-L-Ala-L-Ala-aa-SBzl were used for this study. Inspection of FIG. 1 reveals a strong preference for the straight and branched aliphatic side chains. Aromatic and sulfur- and oxygen-containing side chains are poor binders by this criteria. This approach can also employ irreversible inhibitors in which Z is an activating group such as chloroalkyl instead of a chromogenic leaving group.

Of course, those skilled in the art recognize that residues other than P1 also contribute to the binding interaction between enzyme and inhibitor. Thus, the choice of a P1 which meets the geometric requirements for the reactive site geometry may not be entirely sufficient if other reactive site residues have a significant role for a particular target serine protease.

The sequence outside of the reactive site is necessary to achieve and maintain the proper tertiary fold required for inhibitory activity. The proper spacing of half-cystine residues is well conserved. As with many other families of homologous proteins it follows that the disulfide pairings are also likely conserved and can be expected to play a role in the maintenance of the active three-dimensional structure. this region can then be appropriately termed a "molecular scaffolding" or "framework".

The atomic structures of serine protease inhibitors that have thus far been determined reveal a great deal of similarity in the region of the reactive site. Similarly, X-ray crystal structures of serine proteases have revealed extensive structural similarity in the active site. It is reasonable to expect that residues within the reactive site of protease inhibitors of the present invention will have to meet certain geometrical requirements in order to exhibit inhibitory activity. It follows that any sequence variations made in reactive site will have to conformationally allow the required reactive site geometry. Substitutions which fail to allow this requirement will fail to inhibit.

It is to be expected that substitutions can be tolerated if they do not interfere with the attainment and stability of the tertiary fold. Other natural (both those occurring and not naturally occurring in protein) or synthetic amino acids may be substituted into these polypeptides when their side chains provide the functional identity needed to maintain peptide structure and function. For example, ornithine is a basic amino acid that may substitute for Lys, Arg or His. β-2-thienylalanine is a synthetic amino acid which is a phenylalanine analogue. Of course, appropriate stereoisomers of the amino acids could be substituted, provided the biological activity is not adversely affected. Certain deletions may likewise be possible although these may be unlikely due to the small size of these polypeptides. It may also be possible to further stabilize the fold by adding more disulfide bonds or adding groups which can form salt bridges or hydrogen bonding donor/acceptor pairs. The existing bridges may be eliminated if they are compensated for by the addition of new disulfide bridges, salt bridges, hydrogen bond pairs or any appropriate combination.

Those skilled in the art will recognize that the peptide inhibitors of the present invention may be chemically modified. For example, the amino-terminus and/or lysine residues might be acylated. Alternately, the carboxyl groups might be esterified or amidated. Extensions to the amino- or carboxy-termini, either separately or simultaneously, are possible. Such extensions may contain other desirable properties such as another inhibitor molecule or perhaps a molecular recognition segment for targeting to a particular tissue. An example of a molecular recognition segment would be a polypeptide hormone which serves as a ligand for a receptor. Another example would be an antibody.

For purposes of the present invention two peptide sequences are considered to be homologous variations of one another if the two sequences exhibit at least 75% likeness in amino acid identity and/or similarity. This comparison may be made using one of several available algorithms. An example of a suitable algorithm is that of Lipman and Pearson (Science, 227, 1435-1441 [1985]). This algorithm is available in the form of the computer program FASTP (W. R. Pearson, Department of Biochemistry, University of Virginia, Charlottesville, Va. 22908). Those skilled in the art recognize that substitutions, deletions and insertions of amino acids are frequently observed in proteins and polypeptides without untoward effects on structure and function. Indeed, the polypeptide inhibitors listed in Table I exhibit at least 75% sequence identity. For example, polypeptides 2-7, 43 and 44 are considered to be homologous variations of polypeptide 1; polypeptides 9-14 are considered homologous variations of polypeptide 8; polypeptides 16-21 are considered homologous variations of polypeptides 15; polypeptides 23-28 are considered homologous variations of polypeptide 22; polypeptides 30-35 are considered homologous variations of polypeptide 29; polypeptides 37-42 are considered homologous variations of polypeptide 36 and polypeptides 52-57 are considered homologous variations of polypeptide 51.

Those skilled in the art further recognize that homology is only an indication of structure and function. That is, not every combination of insertions, deletions and substitutions resulting in a homology score greater than 75% sequence identity will necessarily result in a biologically active polypeptide. For example, the positions of the half-cystines are typically highly conserved in protease inhibitors with only slight shifts in positions being observed. Hence, the above described homology criteria should be met with the qualification that the peptide retain a substantial degree of its inhibitory activity.

The polypeptides of Table II are quite homologous. All have a proline residue at P2. The well known propensity of proline to occur in a chain reversal may explain its strict conservation. While proline may be required at P2, it should be recognized that other residues also have a relatively high frequency of occurrence at chain reversals, specifically, glycine followed by aspartic acid, asparagine and serine. Published results with small peptide substrates have indicated that alanine and leucine may also function at the P2 position. The half-cystine at position P3 is strictly conserved. A half-cystine at position P3 may be a requirement in order to maintain the proper disulfide pairing and overall conformation. The P4 position is occupied by either of the non-polar residues valine and methionine in the squash family of inhibitors. Other polar and non-polar substitutions at P4 may be possible. Insofar as the substitutions do not interfere with the attainment of the necessary overall fold and the reactive site geometry, the effects of the substitutions will depend on the target serine protease. The P5 position is occupied by either arginine or methionine in the squash family of inhibitors. The same comments made regarding the P4 position apply.

The pattern for P1' to P5', i. e., three successive non-polar residues followed by charged residue followed by half-cystine, is strictly conserved within the known members of the squash family of inhibitors. Sequence variants in the P1' to P5' positions can be expected to influence more or less the affinity and selectivity of a peptide depending on the substitution and the target serine protease. For example, both positively (lysine) and negatively (glutamic acid) charged residues are observed at position P4' with little difference in the equilibrium association constant. On the other hand, P5' is Cys in all polypeptides and may be a requirement for proper disulfide pairing.

Members of the squash family of inhibitors have few changes within the framework region of the sequence. It should be recognized that substitutions are found. This is entirely consistent with assignment of this portion of the sequence as a framework given the low frequency and conservative nature of the substitution.

The sequences of these trypsin inhibitors are highly conserved. The degree of homology between these inhibitors and their substantially equivalent binding constants for trypsin directly supports the homology criteria described above with respect to the polypeptide inhibitors of the present invention.

The polypeptides of the present invention are useful in a variety of situations such as therapeutic agents, control of serine protease activity in fermentation broths and, possibly pest control.

The polypeptides of the present invention are useful as agents in the treatment or, where appropriately indicated, the prevention of pathological situations associated with unwanted protease activity. Appropriate uses exist in both human and veterinary medicine. The polypeptides may be administered as free polypeptides or pharmaceutically acceptable salts thereof. The term "pharmaceutically acceptable salt" refers to those acid addition salts or metal complexes of the polypeptides which do not significantly or adversely affect the therapeutic properties (e.g. efficacy, toxicity, etc.) of the polypeptides. The polypeptides should be administered as a pharmaceutical composition which, in most cases, will comprise the polypeptide and/or pharmaceutical salts thereof with a pharmaceutically acceptable carrier. The term "pharmaceutically acceptable carrier" refers to those solid and liquid carriers which do not significantly or adversely affect the therapeutic properties of the polypeptides. The pharmaceutical compositions containing polypeptides of the present invention may be administered to humans either intravenously, subcutaneously, intramuscularly, intranasally or even orally. The necessary dosage will vary with the particular condition being treated, method of administration and rate of clearance of the polypeptide from the body. In most cases dosages between 0.001 and 30 mg/kg should be effective. A dose range between 0.1 and 10 mg/kg is preferred.

The polypeptides of the present invention are also useful to control levels of protease activity in fermentation broths. They are suitable to protect proteins produced by fermentation of genetically engineered microbes from degradation. This may be accomplished by addition of exogenous polypeptides or by co-cloning and expression of the gene coding for these polypeptides with that of the gene for the protein to be protected.

The polypeptides of the present invention may also be useful for the control of household and agricultural pests by the termination of their digestive function. The polypeptides should be formulated to achieve proper efficacy according to the environment at the site of application. The polypeptides may be used with other pest control agents.

The peptide inhibitors may be prepared by any suitable method. This includes recombinant DNA techniques and chemical synthesis including the widely used solid phase peptide synthesis method of Merrifeld (J. Am. Chem. Soc., 85, 2149 (1963); "Solid Phase Peptide Synthesis", Stewart and Young, Second Ed., Pierce Chemical Co., Rockford, Ill.). The polypeptides of the present invention contain cysteine so that 1 ml of anisole and 150 mg of mercaplopyridine per gram of peptide resin should be included in the standard hydrogen fluoride cleavage reaction. The cleaved peptide is lyophilized from about 15% acetic acid.

The crude peptide is then oxidatively folded in the following manner. Oxidation buffer (0.1M Tris-HCl, pH 8.75 containing 1 mM EDTA, and a mixture of reduced (0.5 to 1.0 mM) and oxidized (5 to 10 mM) glutathiones in a molar ratio of 1 to 10, respectively), is added to the crude peptide to give a concentration of 4 mg/ml of peptide. Any insoluble material is sedimented by centrifugation at 8600 xg for 10 minutes. The supernatant is decanted and the oxidative folding reaction proceeds for 2 to 8 hrs at ambient temperature. The reaction mixture can be stored at 4° C. until the purification step.

The oxidized crude peptide can be analyzed for inhibitory activity against one or more serine proteases using, for example, the assays described below. It is prudent to perform a control using only the oxidation buffer. The oxidized crude peptide can be analyzed by reverse-phase HPLC on a C18 silica gel column using a water-/acetonitrile composition gradient of 20 to 40% acetonitrile in which both solvents contain 0.1% trifluoroacetic acid and a flowrate of 2ml/min. The column effluent is monitored by absorbance at 226 nm. Injection of 200 to 300 μl of oxidized crude peptide allows the collection of peaks for identification of the active component using an appropriate inhibition assay. It also permits the assessment of relative purity, elution time and, hence, the percentage of acetonitrile at the gradient mixer when the peptide elutes from the column. The elution time of the active component is essential for following the purification (see below) using analytical-scale HPLC assay of the chromatographic fractions. The percentage of acetonitrile is useful for establishing the approximate conditions (solvent composition) needed to achieve a purification of the oxidized crude peptide.

The oxidized crude polypeptides of the present invention can be purified in the following manner. The oxidized crude peptide is filtered through a 0.45 μm filter to remove any of the cloudy suspension which is sometimes observed. The filtered solution is pumped at a flow rate of 6ml/min onto a 40×350 mm Michel-Miller glass column filled with C18 silica gel (10 μM). The column has been equilibrated with solvent obtained by mixing acetonitrile and glass-distilled water, both containing 0.1% (v/v) trifluoroacetic acid, to a final composition of 5% acetonitrile. The column is washed with the 5% acetonitrile for 30 to 60 minutes in order to elute any unbound material, a flow rate of 6 ml/min is used for this and all subsequent operations. A gradient is run from 5% acetonitrile to the final composition in 30 minutes. The column is then eluted isocratically at the final composition until the active component has emerged from the column. The column effluent is monitored by absorbance at 226 nm and fractions are collected using a fraction collector. The fractions are assayed for inhibitory activity using the appropriate assays (see below). The active fractions are assayed for purity using analytical-scale reverse-phase HPLC as described above. The fractions are pooled using this information to give greater than 95% homogeneous polypeptide as determined by HPLC. The pooled fractions are lyophilized. The polypeptides are thus obtained as the salt of trifluoroacetic acid.

For the initial attempt at purification it has been observed that a suitable final composition is one that is 10% less in acetonitrile than the percentage at which the peptide eluted from the analytical-scale reverse-phase HPLC. Improvement can then be made by minor adjustments of one to a few percent acetonitrile after examining the initial elution profile.

The inhibitory activity of the polypeptides of the present invention can be easily assayed using in vitro assays. In these types of spectrophotometric assays the activity of the serine protease is measured toward an appropriate p-nitroanilide substrate in the presence and absence of the peptide inhibitor. The enzyme catalyzed hydrolysis of the peptide p-nitroanilide substrate produces p-nitroanaline which results in an increase in absorbance which is monitored in the range of 405 to 410 nm. The rate of increase in absorbance is a measure of the enzymatic activity and the decrease in this rate relative to a suitable control is used to ascertain inhibition. The general assay procedure and details of the particular assays employed in the examples are provided in the Appendix following the examples. It is also possible to test the polypeptides in a functionally oriented assay that emulates in vivo conditions. Such an inhibition assay for elastase is also described in the Appendix.

EXAMPLES 1-15

Exemplary polypeptides of Table I were prepared by solid-phase synthesis and were purified as previously described with the exception of polypeptides 29,36,43,47,48 and 50 which were assayed as oxidized (folded) crude peptide.

A peptide with the sequence of the naturally-occurring trypsin inhibitor shown in the first row of Table II served as a comparative control in this example. The polypeptides listed below were assayed for activity toward trypsin, elastase, cathepsin G and chymotrypsin using the assays described in the following appendix. The results of the assays are listed in Table III below.

TABLE III

| Peptide | Inhibitory Activity | | | |
|---|---|---|---|---|
| | Trypsin | Elastase | Cathepsin G | Chymotrypsin |
| Control | ++ | − | − | − |
| 1 | − | ++ | − | − |
| 8 | − | ++ | − | − |
| 43 | − | ++ | − | − |
| 44 | − | ++ | − | − |
| 15 | ++ | ++ | ++ | ++ |
| 22 | ++ | ++ | + | ++ |
| 29 | ++ | ++ | + | ++ |
| 36 | + | ++ | + | ++ |
| 51 | − | ++ | − | − |
| 45 | − | ++ | − | − |
| 46 | − | ++ | − | − |
| 47 | − | ++ | − | − |
| 48 | − | + | − | − |
| 49 | − | + | − | − |
| 50 | − | − | − | − |

Figure 2:
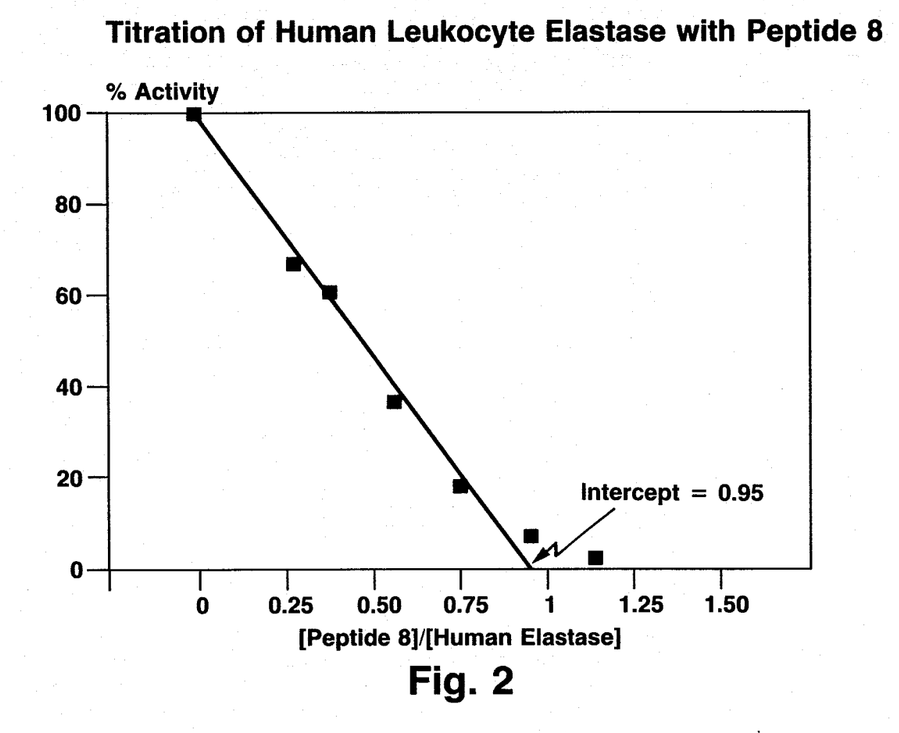
FIG. 2 shows a titration curve for elastase inhibition by inhibitor peptide 8.

++ Represents greater than 50% inhibition
+ Represents between 10% and 50% inhibition
− Represents less than 10% inhibition Peptide inhibitors were assayed at an inhibitor/protease ratio between about 10/1 and 50/1. Peptides exhibiting greater than 50% inhibition at this mole ratio should exhibit essentially complete inhibition at inhibitor/protease ratios of about 100/1. Less effective inhibitors should exhibit substantial inhibition at higher inhibitor/protease ratios. Preferred elastase inhibitors include peptides 1, 8 and 51. Peptide 8 is particularly preferred as an elastase inhibitor. Referring to FIG. 2, peptide 8 exhibits essentially stochiometric inhibition of human elastase.

Referring to FIG. 1 it is clear that elastase has a strong preference for isoleucine (Ile) and valine (Val). The assay data demonstrates that substituting Ile or Val for Arg in the P1 position produces a potent elastase inhibitor. The activity of Peptides 43 through 48 demonstrate that conservative substitutions can be made remote from the P1 position and still maintain the biological activity.

Polypeptide 15 was synthesized in which phenylalanine was substituted at P1. Chymotrypsin and cathepsin G are known to exhibit a preference for phenylalanine at the P1 position. Inhibition of chymotrypsin and cathepsin G was observed. Polypeptide 15 also inhibited human elastase and trypsin. Peptide 22 which, like peptide 15, possesses a bulky non-polar amino acid (Met) at the P1 position also inhibits human cathepsin G, chymotrypsin, human elastase and trypsin. For comparison, the naturally occurring α-1-proteinase inhibitor also has a methionine at the P1 position and likewise inhibits all of these enzymes.

The activity of peptides 45, 46, 47, 48, 29, 36 and 49 demonstrates that peptides having hydrophobic side chains at the P1 position continue to be inhibitors of human elastase. Alanine can be substituted for isoleucine at the P1' position although some differences in potency may result. The fact that peptides 49 and 50 exhibit only marginal activity suggests that the cysteine residue at position P3 is important and substantially invariant. Hydroxyproline (Hyp) and glycine can be substituted for proline at the P2 position demonstrating that amino acids capable of adopting a chain reversal conformation can be substituted for proline in the P2 position.

The fact that peptide 51, which lacks a P1 side chain, is a human elastase inhibitor suggests that the side chain alone is not responsible for inhibition. Peptide 51 is a less effective inhibitor of elastase than peptides 1 or 8. Hence, it follows that the P1 side chain can enhance (Peptide 8) or diminish (trypsin inhibitor control) the inhibition that is conferred by the remainder of the reactive site (peptide 51).

Examples 16–17

In order to demonstrate the usefulness of the inhibitors of the present invention, peptide 8 was tested in additional functional bioassays using more natural and effective substrates. Peptide 8 was also tested using polymorphonuclearleukocytes (PMN) as the source of proteolytic activity.

Figure 3:
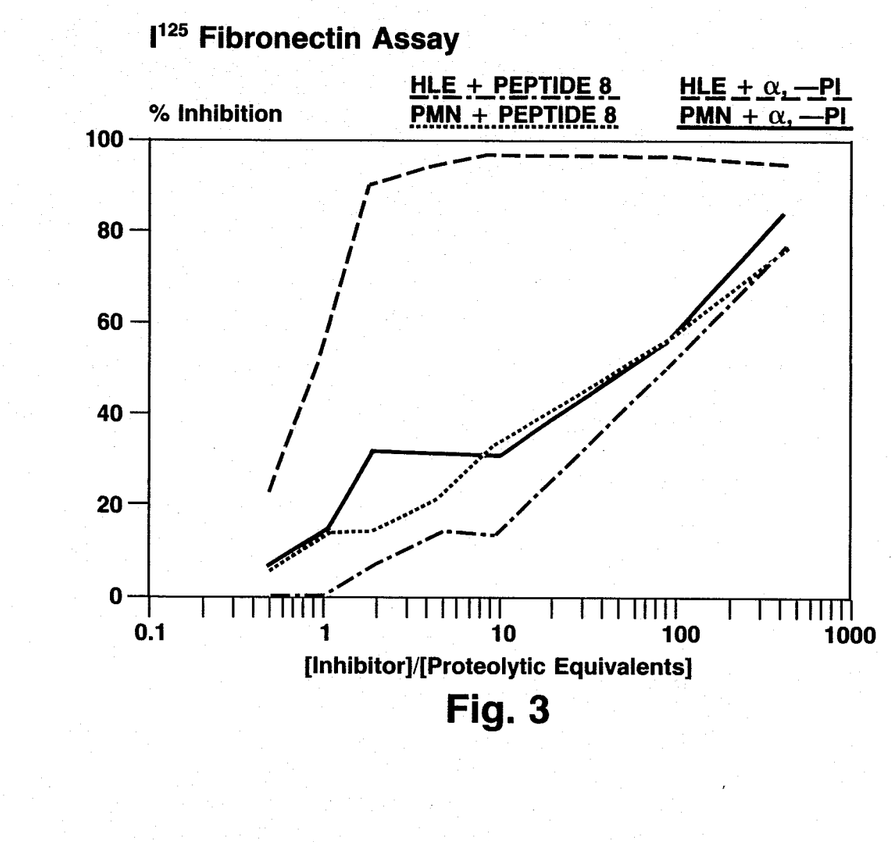
FIG. 3 illustrates the data obtained from the $^{125}I$ fibronectin assay for inhibitor peptide 8.

FIG. 3 illustrates inhibition data obtained using $^{125}I$ fibronectin as substrate at an enzyme concentration of 4 nM (or an equivalent amount of PMN-derived human elastase activity (HLE equivalent)). The data points represent the mean of several (n=3 to 9) replicates compared to the control that contained no inhibitor.

Peptide 8 demonstrated nearly the same inhibitory profile against purified human elastase (HE) and PMN-derived HE activity. The α-1-proteinase inhibitor was much more effective against purified HE than peptide 8. However, when stimulated PMN were used, α-1-proteinase inhibitor's effectiveness dropped to a degree similar to that of peptide 8.

Figure 4:
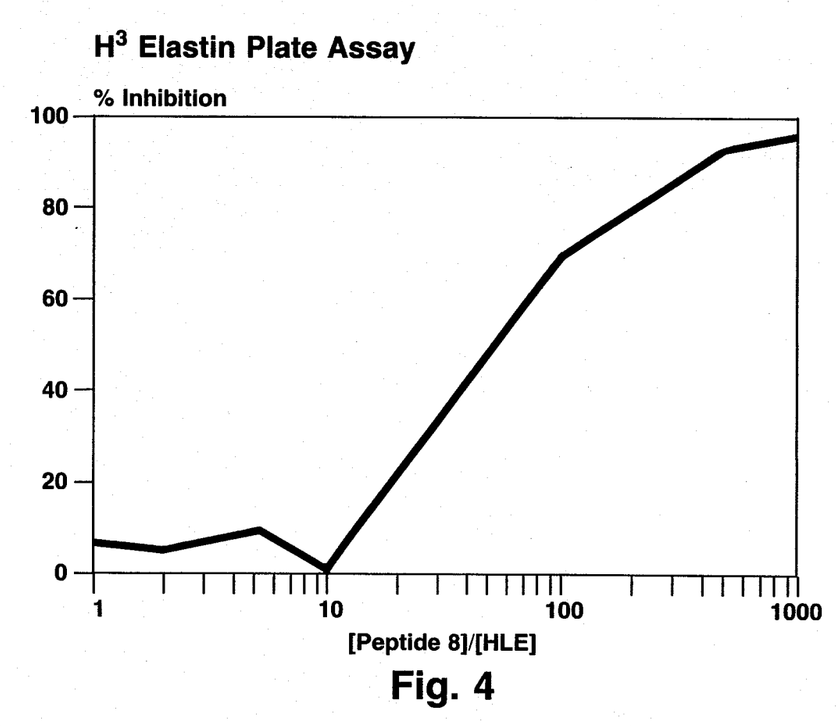
FIG. 4 illustrates the data obtained from the $^{3}H$-elastin assay for inhibitor peptide 8.

The inhibition of elastolysis by peptide 8 was investigated using the $^3H$-elastin assay and purified HE. The results shown in FIG. 4 is similar to FIG. 3 indicating that peptide 8 is equally effecive for these two connective tissue substrates.

APPENDIX

Generalized Protocol Spectrophotometric Assays:

(1) Pipette 100 μl of enzyme solution into a disposable polystyrene cuvette (1 cm optical path length).

(2) Add (1900-X) μl of bufferto the cuvette, where X is the volume of test solution in microliters that is added in the next step.

(3) Add X μl of test solution to the cuvette, where X ranges from 0 μl for the control to a maximum of about 500 μl. Incubate the solution for a period of 1 to 5 minutes at ambient temperature.

(4) Add 100 μl of substrate solution to the cuvette. Mix the contents by covering the cuvette with a piece of paraffin film and repeatedly inverting for a period of 5 to 15 seconds.

(5) Record the change in absorbance for about 5 minutes at either 405 or 410 nm, depending on the assay, with a spectrophotometer equipped with a suitable recording device.

(6) The inhibition is determined by the diminution of the observed initial rate of change in absorbance relative to a control that does not contain test solution. The percent inhibition is calculated from the formula $$\% \text{ Inhibition} = 100 \times \left[ 1 - \frac{(\Delta A/\text{min}) \text{ test}}{(\Delta A/\text{min}) \text{ control}} \right]$$

where (ΔA/min) is the initial rate of absorbance change.

(7) For more accurate quantitative determinations temperature control of the cuvette holders and the reagent solutions can be instituted.

(8) The test solution can be crude oxidized peptide prepared as described above, fractions from a chromatographic separation or purified polypeptides.

Trypsin Assay (A) Buffer Solution - Triethanolamine buffer consisting of 200 mM triethanolamine, 20 mM CaCl$_2$, pH 7.8

(B) Substrate solution - Dissolve 50 mg of N-Benzoyl-L-arginine p-nitroanilide in 50 ml of water. Sonicate for 5 to 10 minutes to completely dissolve the solid material.

(C) Enzyme solution - Dissolve 1 mg of bovine trypsin in 10 ml of 0.001N HCl stored on ice during the assay.

(D) Test Solution - See general protocol, number 8.
Procedure: Use the above solutions in the general protocol described above.

Cathepsin G Assay (A) Buffer Solution - Tris-NaCl buffer consisting of 0.1M Tris-HCl, pH 8.0 containing 0.5M NaCl and 0.03% sodium azide.

(B) Substrate solution - Dissolve 50 mg of N-succinyl-L-alanyl-L-alanyl-L-prolyl-L-phenylalanine p-nitroanilide in 1 ml of 1-methyl-2-pyrrolidinone and dilute to 50 ml with Tris-NaCl buffer.

(C) Enzyme Solution - Human Sputum Cathepsin G (Product No. SG-45, EPC, Inc., Pacific, Mo.). Dissolve 1 mg of protein per 1 ml of Tris-NaCl buffer. Store on ice or at 4° C.

(D) Test Solutions - See the general protocol, number 8.

Procedure: Use the above solution in the general protocol described above.

(1) This assay may be used for chymotrypsin by substituting the enzyme solution of the chymotrypsin assay.

Chymotrypsin Assays (A) Buffer solution - triethanolamine buffer- See trypsin assay.

(B) Substrate Solution - Dissolve 25 mg of 3-carbomethoxypropionyl-L-arginyl-L-prolyl-L-tyrosine p-nitroanilide (Product No. S-2586, KabiVitrum AB, Stockholm, Sweden) in 23.6 ml of water (C) Enzyme solution - Dissolve 1 mg of bovine chymotrypsin in 4 ml of 0.001N HCl. Prepare the final dilution by combining 0.1 ml of the stock chymotrypsin solution and 10 ml of 0.001N HCl. Store on ice or at 4° C.

Procedure: Use the above solutions in the general protocol (2) See note 1 of the cathepsin G assay.

(3) 0.1M Tris-HCl, pH 7.8, 20 mM $CaCl_2$, 0.05% triton X-100 can be substituted for the triethanolamine buffer.

Elastase Assays

Method 1:

(A) Buffer Solution - Tris-NaCl buffer consisting of 0.1M Tris-HCl pH 7.5 at 25° C. containing 0.5M NaCl and 0.01% (w/v) $NaN_3$.

(B) Substrate Solution - Dissolve 45.5 mg of N-succinyl-L-alanyl-L-alanyl-L-alanine p-nitroanilide in 1 ml of 1-methyl-2-pyrrolidinone. Add 32 ml of Tris-NaCl buffer.

(C) Enzyme Solution - Human Sputum Elastase, product No. SE-563 EPC, Inc., Pacific, Mo. USA, Lot 85701. Dissolve 1 mg in 1 ml of Tris-NaCl buffer. Store on ice or at 4° C.

(D) Test Solution - See general protocol, number 8.

Procedure: Use the above solutions in the general protocol described above.

Method 2:

(1) Buffer Solution - Tris-NaCl buffer -see Method 1.

(2) Substrate Solution - Dissolve 50 mg of 3-carbomethoxypropionyl-L-alanyl-L-alanyl-L-propyl-L-valine p-nitroanilide in 1 ml of 1-methyl-2-pyrrolidinone. Add 32 ml of Tris-NaCl buffer.

(3) Enzyme Solution - Human sputum elastase, product No. SE-563, EPC, inc. Pacific, Mo. USA, Lot 85071. Prepare a sample at a concentration of 0.01 mg per ml of Tris-NaCl buffer. Store on ice.

(4) Test Solution - general protocol, number 8.

Procedure: Use the above solutions in the general protocol.

(1) Porcine pancreatic elastase may be substituted for human elastase when it is desired to test for an inhibitor of the former.

(2) The activity of an elastase preparation can be calculated as $$\text{Activity} = \frac{(\Delta A \text{ (410 nm)/min.}) \times 340.0}{(\text{Volume of elastase added}) \times (\text{Conc. of elastase})}$$

(3) The Tris-NaCl buffer also can be pH 8.0 with 0.03% sodium azide. Results should be compared at a single pH.

Functional Assay for Elastase Inhibition

Elastase Diffusion Plate Assay

Elastolytic activity is measured by the radial solubilization of fluorescein-impregnated elastin particles suspended in a thin film of cast agar. The area of the clearing zone is proportional to the amount of elastase added to a well cut into the agar. Peptides can be tested for the ability to inhibit the clearing of a zone.

Materials and Reagents:

(1) Alphasin elastase diffusion plate, product No. A-622, EC, Inc., Pacific, Mo., Lot. No. 86128.

(2) Human Sputum Elastase, EPC, Inc., Pacific, Mo., Product No. SE-563 Prepare at a concentration of about 300 units/ml (determined using method 1 of the spectrophotometric assay for elastase) in Tris-NaCl buffer (method 1).

(3) Test Solution - Peptides at a concentration of about 1 ug/µl.

Procedure:

(1) Add 10 µl of the elastase solution to 1.5 ml Eppendorf tubes (1 tube for a control and 1 tube for each test solution).

(2) Add (20-X) µl of Tris-NaCl buffer, where X is the volume in microliters of the test sample added.

(3) Add X µl of test solution, where X is between 0 and 20. Incubate for 1 to 5 minutes at ambient temperature.

(4) Assay 10 µl of the resulting solution using Method 1, except that only 10 µl of enzyme solution is used in the first step.

(5) Pipette 10 µl of each sample into a well.

(6) Incubate at 37° C. for 12 hours.

(7) The area of the clearing zones is conveniently read with an antibiotic zone reader. The area of the well (control) is subtracted from each value.

Notes for Elastase Diffusion Plate Assay (1) Care must be taken to avoid dehydration of the agar during the incubation. The plate is placed in a plastic bag along with a few ml of water and the bag is sealed.

(2) See note 1 for Method 1.

(3) The inhibition is determined according to the formula $$\% \text{ Inhibition} = 100 \left[ 1 - \frac{(\text{Corrected Area}) \text{ Test}}{(\text{Corrected Area}) \text{ Control}} \right]$$

$^{125}$I-Fibronectin Assay

This assay is designed to model the degradation of connective tissue. The assay is carried out essentially as described by Campbell, et al. (J. Clin. Invest., 1982, 70:845–52). Briefly, purified human plasma fibronectin (fn) is radiolabeled with $^{125}$I using Enzymobeads and conventional procedures. The desalted is diluted with fn to yield ca. cpm/ug. This material is further diluted with pH 9.6 barbital buffer and 200 ul (30 ug fn, 50000 cpm) is pipetted into the wells of a flat bottomed 96 well microtiter plate. The plates are dried for about 24 hours at 37° C. and unbound fn is removed with 2 washes of phosphate buffered saline (PBS). The plates are stored at 4° C. and are stable for at least 2 weeks.

For an assay each coated well is filled with a total volume of 200 μl. All measurements are carried out at optimal pH and buffer conditions. After addition of proteolytic activity with or without inhibitor the plate is incubated at 37° C. for 3 hours. The well contents are centrifuged and a 100 μl aliquot is counted for 125I gamma radiation. Some assays employed elastase activity derived from freshly prepared neutrophils (PMN). In this case an activating agent to stimulate the PMN is present in the well and the PMN is added last. A standard curve showing the linearity of the response to the amount of purified human elastase (HE) added is obtained concurrently with each assay.

³H-Elastin Assay

Another, yet less sensitive, assay employs radiolabelled elastin as the solid substrate in order to imitate degradation of connective tissue.

Radiolabeling of bovine neck ligament elastin is carried out with tritiated sodium borohydride as described by Stone, et al. (Anal. Biochem., 1977, 80:572–577). Elastin coated microtiter plates are prepared essentially as described above for the fibronectin plates. The assay is run similarly except that the supernatant is added to a scintillation cocktail for counting. The linearity of the responses to purified HE is also tested.

We claim:

1. A synthetic serine protease inhibitor having the following sequence:

Arg—Val—Cys—Pro—X—Ile—Leu—Met—Lys—Cys—Lys—

Lys—Asp—Ser—Asp—Cys—Leu—Ala—Glu—Cys—Val—

Cys—Leu—Glu—His—Gly—Tyr—Cys—Gly which exhibits inhibitory activity towards elastase in which X is selected from the group consisting of isoleucine, norvaline, valine, norleucine, methionine, leucine, alanine, glycine and phenylalanine.

2. A serine protease inhibitor of claim 1 in which X is valine.

3. A serine protease inhibitor of claim 1 in which X is iosleucine.

4. A serine protease inhibitor of claim 1 exhibiting inhibitory activity toward elastase and cathepsin G in which X is phenylalanine.

5. A serine protease inhibitor of claim 1 exhibiting inhibitory activity toward elastase and cathepsin G in which X is methionine.

6. A serine protease inhibitor selected from the group consisting of

7. A pharmaceutical composition for inhibiting a target serine protease containing an effective amount of an inhibitor of claim 1 or a pharmaceutically acceptable salt thereof and a pharmaceutically acceptable salt thereof and a pharmaceutically acceptable carrier therefor.

8. The composition of claim 7 in which X is valine.

9. The composition of claim 7 in which X is isoleucine.

10. The composition of claim 7 in which X is phenylalanine.

11. The composition of claim 7 in which X is methionine.

12. A method for treating an individual having a physiological condition caused by unwanted serine protease activity which comprises administering to the individual a therapeutically effective amount of an inhibitor of claim 1.

13. The method of claim 12 in which X is valine.

14. The method claim 12 in which X is isoleucine.

15. The method of claim 12 in which is phenylalanine.

16. The method of claim 12 in which X is methionine.

17. A pharmaceutical composition for inhibiting a target serine protease containing an effecting amount of an inhibitor of claim 6 or a pharmaceutically acceptable salt thereof and a pharmaceutically carrier therefor.

18. A method for treating an individual having a physiological condition caused by unwanted serin protease activity which comprises administering to the individual a therapeutically effective amount of an ihibitor of claim 6.

* * * * *